United States Patent
Hettrick et al.

(10) Patent No.: US 8,700,155 B2
(45) Date of Patent: Apr. 15, 2014

(54) SYSTEM AND METHOD FOR USING ATRIAL PACING TO ENHANCE FUNCTION OF STUNNED ATRIAL MYOCARDIUM FOLLOWING CONVERSION TO NORMAL SINUS RHYTHM

(75) Inventors: Douglas A. Hettrick, Blaine, MN (US); David E. Euler, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 1255 days.

(21) Appl. No.: 11/095,846

(22) Filed: Mar. 31, 2005

(65) Prior Publication Data
US 2006/0224201 A1 Oct. 5, 2006

(51) Int. Cl.
*A61N 1/365* (2006.01)

(52) U.S. Cl.
USPC .................................. 607/27; 607/11; 607/14

(58) Field of Classification Search
USPC ................................. 607/11, 14, 27
See application file for complete search history.

(56) References Cited

U.S. PATENT DOCUMENTS

| | | | | |
|---|---|---|---|---|
| 5,213,098 | A | 5/1993 | Bennett et al. | 128/419 PG |
| 6,058,328 | A | 5/2000 | Levine et al. | 607/14 |
| 6,134,470 | A * | 10/2000 | Hartlaub | 607/14 |
| 6,185,459 | B1 * | 2/2001 | Mehra et al. | 607/14 |
| 6,292,694 | B1 | 9/2001 | Schloss et al. | 607/9 |
| 6,411,847 | B1 | 6/2002 | Mower | 607/9 |
| 6,526,317 | B2 * | 2/2003 | Hsu et al. | 607/4 |
| 6,606,517 | B1 * | 8/2003 | Park et al. | 607/14 |
| 2002/0099414 | A1 | 7/2002 | Evers et al. | 607/14 |
| 2003/0130703 | A1 | 7/2003 | Florio et al. | |
| 2003/0144698 | A1 | 7/2003 | Ujhelyi et al. | |
| 2003/0199932 | A1 * | 10/2003 | Struble | 607/14 |
| 2003/0233130 | A1 | 12/2003 | Padmanabhan et al. | 607/9 |
| 2004/0049235 | A1 | 3/2004 | Deno et al. | 607/9 |
| 2004/0088010 | A1 | 5/2004 | Warman et al. | |

FOREIGN PATENT DOCUMENTS

| | | | | |
|---|---|---|---|---|
| WO | WO 02/45792 | A2 | 6/2002 | |
| WO | WO 02/53026 | A2 | 7/2002 | A61B 5/00 |

OTHER PUBLICATIONS

Gaasch et al., "Potentiation of Atrial Contractility by Paired Pacing Augments Ventricular Preload and Systolic Performance," *J Cardiac Fail.*, vol. 8, p. 141-6 (2003).

Sanders et al., "Reversal of Atrial Mechanical Dysfunction After Cardioversion of Atrial Fibrillation," *Circulation*, vol. 108, p. 1976-1984 (2003).

Arbel et al., "Successful Treatment of Drug-Resistant Atrial Tachycardia and Intractable Congestive Heart Failure with Permanent Coupled Atrial Pacing," *Amer J of Cardiol.*, vol. 41, Issue 2, p. 336-340 (Feb. 1978).

(Continued)

*Primary Examiner* — Tammie K Heller
(74) *Attorney, Agent, or Firm* — Michael C. Soldner

(57) ABSTRACT

An implantable medical device (IMD) having a therapy circuit for delivering atrial pacing and a control circuit for detecting a return to sinus rhythm. The control circuit determines the duration of an atrial arrhythmia preceding the return to sinus rhythm, and controls the therapy circuit to deliver transient atrial pacing based on the atrial arrhythmia duration.

20 Claims, 3 Drawing Sheets

(56) References Cited

OTHER PUBLICATIONS

Takagi M. et al.: "Acute improvement of atrial mechanical stunning after electrical cardioversion of persistent atrial fibrillation: comparison between biatrial and single atrial pacing"; Heart (British Cardiac Society) Jan. 2005; vol. 91, No. 1., Jan. 2005, pp. 58-63.

Sanders, Prashanthan et al.: "Reversal of atrial mechanical dysfunction after cardioversion of atrial fibrillation: implications for the mechanisms of tachycardia-mediated atrial cardiomyopathy"; Circulation, Oct. 21, 2003; vol. 108, No. 16, pp. 1976-1984.

* cited by examiner

SYSTEM AND METHOD FOR USING ATRIAL PACING TO ENHANCE FUNCTION OF STUNNED ATRIAL MYOCARDIUM FOLLOWING CONVERSION TO NORMAL SINUS RHYTHM

BACKGROUND OF THE INVENTION

The present invention relates to implantable medical devices (IMDs) that use a method for pacing a heart after an arrhythmia of a sustained duration to reduce the risk of stroke.

Arrhythmias are disorders of the regular beating of the heart. Irregular rhythms originating in one of the upper chambers of the heart, or atria, are called atrial arrhythmias, which include both atrial fibrillation and atrial flutter. One particular problem that can arise from a sustained period of atrial arrhythmia is the formation of blood clots, or thrombosis.

During atrial fibrillation, the heart's upper chambers quiver instead of beating effectively. Because blood is not pumped completely out of the atria during atrial fibrillation, blood may pool inside the atria, and a blood clot, or thrombus, may form on an atrial wall. When the normal heartbeat, or sinus rhythm, resumes, either spontaneously or through medical intervention, there is a danger that a blood clot that has formed in the left atrium will be dislodged. If a blood clot breaks free, it may become lodged in a blood vessel and cause a blockage, or thromboembolism, which may lead to stroke.

Since blood clots take time to form, there is a particular danger of thrombosis following arrhythmias of a sustained duration of time. Doctors seeking to treat patients by converting an irregular heart rhythm to a normal heart rhythm (cardioversion) must determine how long the arrhythmia has been taking place. If the patient's tachyarrhythmia has been for a sustained duration of time, usually defined as 48 hours or more, doctors may prescribe a blood thinning drug, such as heparin or warfarin, to dissolve any blood clots that may have formed. Cardioversion therapy is thus postponed until completion of the pharmacologic regimen.

A problem associated with cardioversion is early recurrence of atrial fibrillation (ERAF), which, as the name implies, means that the atrial fibrillation returns shortly after a sinus rhythm is achieved. Currently, implantable devices that provide high-energy shock therapy for termination of atrial fibrillation (such as the GEM III AT made by Medtronic, Inc.) and low-energy therapies for termination of atrial fibrillation (such as the GEM III AT and AT500 made by Medtronic, Inc.) are limited by ERAF. The risk of ERAF can be minimized by applying short-term, or transient, overdrive pacing. Overdrive pacing is a type of pacing therapy that paces the right atrium at a rate that is higher than the intrinsic heart rate.

Currently devices like the GEM III AT, AT500 and Kappa 900 (another device made by Medtronic, Inc.) include a feature called Post Mode Switch Overdrive Pacing (PMOP) that provides transient, high-rate overdrive pacing when a sinus rhythm is detected after an atrial arrhythmia. PMOP may decrease the risk of ERAF, but it is not intended to address two other problems that arise after cardioversion of an arrhythmia: stunned atrial myocardium and spontaneous echo contrast (SMOKE).

When a person suffers an arrhythmia for a sustained duration of time, the contractibility of the atria is depressed. This phenomenon is known as "stunned atrial myocardium". During this period of time between the end of an arrhythmia and some later time when the patient has fully recovered, there is still a high risk of thrombosis. Spontaneous echo contrast (SMOKE) is a clinical parameter that is associated with this risk of thrombosis. It has been found that during this period of atrial myocardial stunning, applying high-rate atrial overdrive pacing resulted in a lower incidence of SMOKE, and therefore, presumably a lower risk of stroke. Sanders et al., "Reversal of Atrial Mechanical Dysfunction After Cardioversion of Atrial Fibrillation" (Circulation. 2003; 108:1976-1984).

Another type of atrial pacing is paired pacing (or coupled pacing), which is a pacing therapy that augments the contractility of the chambers of the heart. After termination of an arrhythmia, the heart requires a period of time until it fully recovers. Particularly, the cells of the heart exhibit a reduced capacity to contract, and as a result of this depressed contractility there is an increased risk of stroke. Paired pacing is the application of a pair of closely coupled pulses: an initial pulse and a second pulse just outside of the refractory period of the beat evoked by the initial pulse. Paired pacing increases the contractility of atrial tissue and reduces the time needed for atrial contractility to return to its normal state.

Hemodynamic sensor feedback has been used along with paired pacing, such as the device and method disclosed in U.S. Pat. No. 5,213,098. Also, a recent study demonstrated that atrial paired pacing may augment the function of the left ventricle function by improving atrial function and therefore augmenting ventricular filling. Gaasch et al., "Potentiation of Atrial Contractility by Paired Pacing Augments Ventricular Preload and Systolic Performance" (J Cardiac Fail. 2003; 8: 141-6).

Implantable devices that are capable of applying high rate overdrive pacing or paired pacing are known in the art. Using sensors to provide physiological feedback during pacing is also known. However, there is currently no implantable device that applies overdrive pacing or paired pacing in order to reduce the risk of stroke that occurs after a sustained period of atrial fibrillation. Also, there is also no implantable device that uses feedback from hemodynamic sensors to determine appropriate pacing parameters.

BRIEF SUMMARY OF THE INVENTION

The present invention is an IMD that uses transient atrial pacing after cardioversion of arrhythmias of a sustained duration of time to augment atrial mechanical function, reduce the risk of thrombosis in the left atrium, and reduce the risk of stroke.

DETAILED DESCRIPTION

Figure 1:
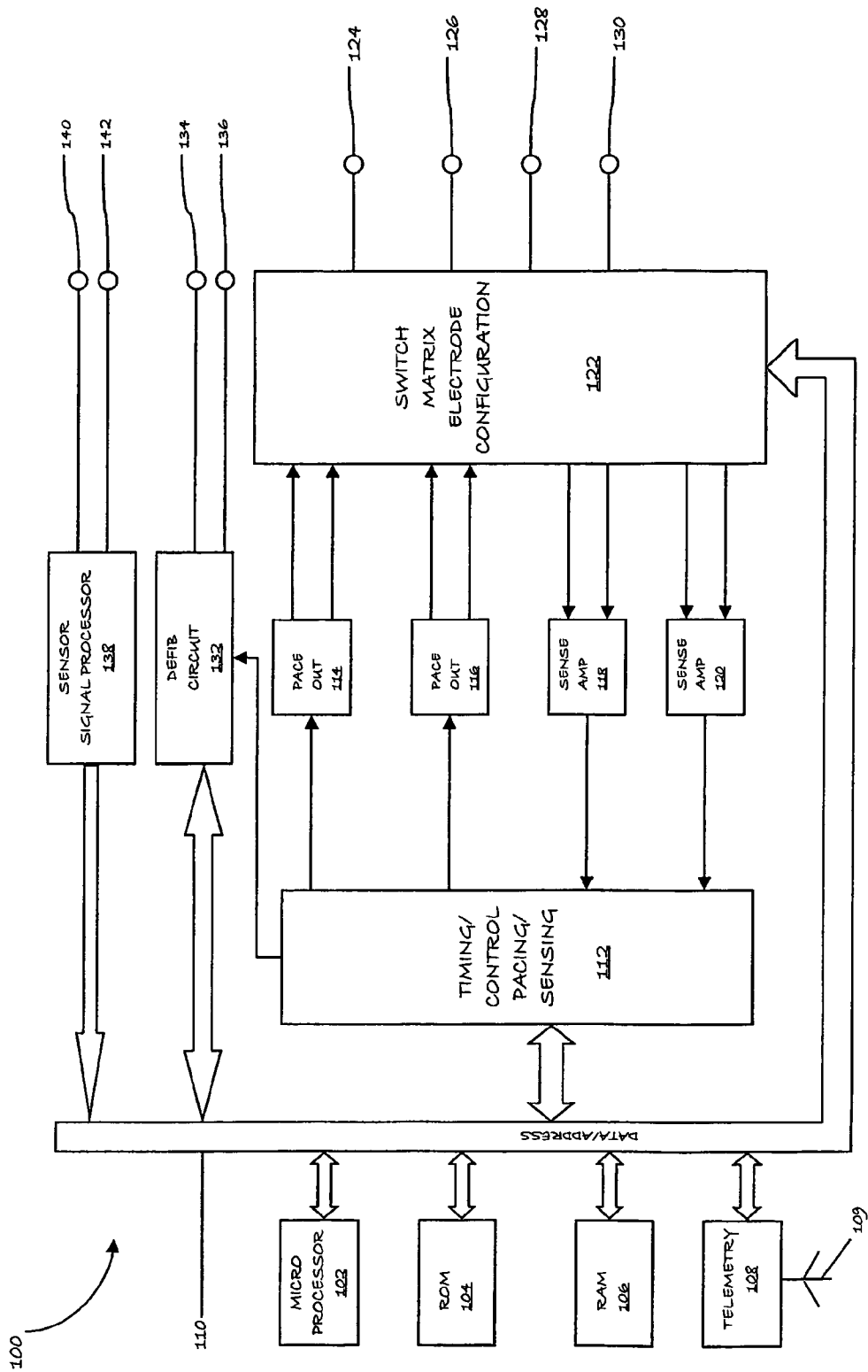
FIG. 1 is a simplified block diagram of electronic components in an implantable medical device that is configured to apply pacing and use sensor feedback.

FIG. 1 is a block diagram of electronic components of an implantable medical device (IMD) 100 that is configured to apply pacing and use sensor feedback. Microprocessor 102 controls the IMD in response to programmed instructions read from a storage device such as read-only memory (ROM)

104 via data/address bus 110. IMD 100 also includes random access memory (RAM) 104, which may be used to store physiological signal data, such as data obtained from tachyarrhythmia episodes. This data may be used by microprocessor 102 for therapy delivery and diagnostic purposes, as will be discussed in more detail in connection with FIGS. 2 and 3. This data may also be transferred to an external device via telemetry circuit 108 and antenna 109. Telemetry circuit 108 and antenna 109 may also be used to transfer information to the IMD.

Microprocessor 102 is coupled to timing/control circuitry 112 and controls timing/control circuitry 112 to deliver pacing pulses to a patient at the appropriate times. These pacing pulses are delivered via output circuits 114 and 116. Timing/control circuit 112 is also coupled to sense amplifiers 118 and 120. Switch matrix 122 selectively couples the pace output circuits 114 and 116 and sense amplifiers 118 and 120 with electrodes 124, 126, 128 and 130.

Defibrillation circuit 132 is able to deliver electrical cardioverting therapy via high voltage capacitors and a charging circuit (not shown). Timing/control circuitry 112 controls the time that defibrillation circuit 132 delivers the electrical cardioverting therapy to an atrium via high-voltage electrode 134 after an atrial arrhythmia is detected by electrode pair 124 and 126. Defibrillation circuit 132 could be further coupled to one or more additional high-voltage electrodes such as electrode 136 positioned on or within a ventricle.

Sensor signal processor 138 receives signals from sensors 140 and 142, which are positioned in the body. Sensors 140 may, for example, be located in the heart to detect parameters such as the oxygen content of the blood, or the carbon dioxide content of the blood. Sensor 142 may, for example, be a hemodynamic sensor that detects parameters such as blood flow, chamber pressure or chamber volume. It may be placed in the heart or in another part of the body, such as systemic or pulmonary arteries and veins.

Sensor signal processor 138 is connected to microprocessor 102 via data/address bus 110. Microprocessor 102 uses the information contained in the signals sent from sensor signal processor 138 to make decisions as to the therapy to deliver to the patient. It may also use data stored in RAM 106, such as the length of a tachyarrhythmic episode, to make decisions as to the therapy to deliver to the patient. Pacing, such as overdrive pacing or paired pulse pacing, may be delivered to the patient via timing/control circuit 112. The present invention, as discussed in detail with respect to FIG. 2 and FIG. 3, relates to the manner in which microprocessor 102 makes decisions regarding therapy to be delivered after cardioversion of an arrhythmia of sustained duration in order to reduce the risk of stroke.

Figure 2:
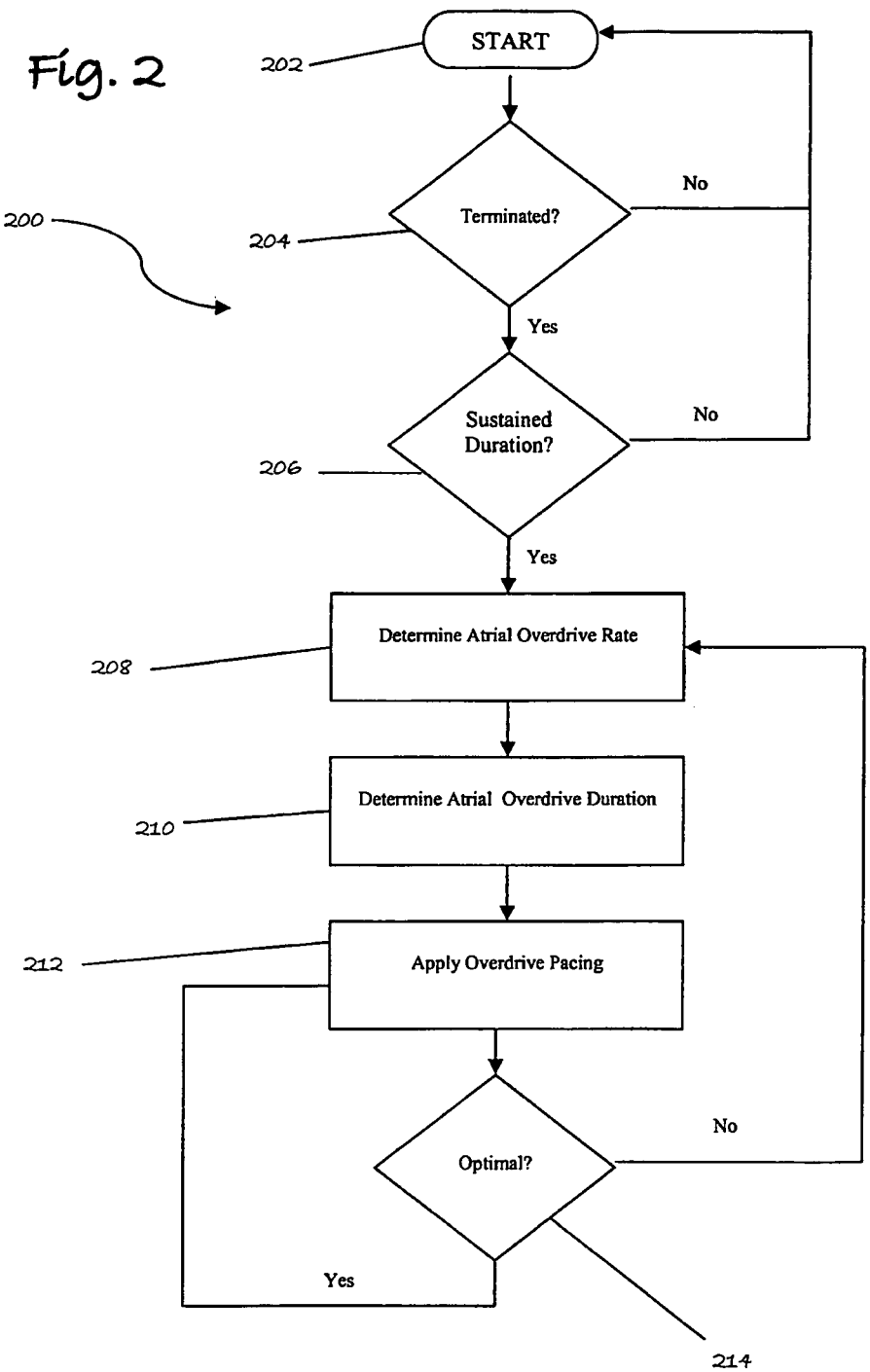
FIG. 2 is a flow diagram illustrating the manner of using transient overdrive pacing after cardioversion of arrhythmias of a sustained duration of time to reduce the risk of stroke according to an embodiment of the invention.

FIG. 2 shows a flow chart for a process 200 of applying transient, constant rate atrial overdrive pacing after cardioversion of an arrhythmia of a sustained duration to augment atrial mechanical function and reduce the risk of stroke. The process illustrated in FIG. 2 begins at start box 202. Because the process is applied after termination of atrial arrhythmia, decision box 204 determines whether an arrhythmia has terminated. If the arrhythmia has not terminated, the process returns to start box 202; if the arrhythmia has terminated, the process moves on to decision box 206.

Decision box 206 determines whether the episode of atrial arrhythmia occurred for a sustained duration of time. The definition of sustained duration of time could be selected and entered by the caregiver, or alternatively, it could be predetermined and programmed into the device. The duration of time may be defined as the length or percentage of time of a single episode of atrial arrhythmia, or alternatively, as the cumulative length of time of multiple IMD detected arrhythmia during a certain period of time, such as 80%, or 22 hours out of the last 24 hours. If the measured duration of time of the arrhythmia is less than the amount of time defined as a sustained duration of time, the process returns to decision box 204. If the measured duration of time of arrhythmia meets or exceeds the threshold amount of time defined as a sustained duration of time, the process advances to step 208.

Step 208 determines the overdrive pacing rate. The overdrive pacing rate of the device may be a stored setting, or it could be selected and entered into the device by a caregiver, or it may be variable based on feedback from sensors connected to the device. For example, the device may apply a series of incremented overdrive pacing rates to the patient. During the time that the incremented overdrive pacing rates are applied, a sensor measures a relevant hemodynamic parameter, such as atrial pressure. Hemodynamic information could also be measured directly by the IMD, or information could be transmitted to the device from another IMD or other device via telemetry. After the series of incremented overdrive pacing rates has been applied, the device selects the overdrive pacing rate that corresponds to the minimized value of the mean atrial pressure as the optimal rate. Other hemodynamic variables could be in used in place of, or in addition to, atrial pressure to select the pacing rate, such as arterial pressure, ventricular pressure, mitral valve blood flow, aortic blood flow, left ventricular volume, left ventricular dimensions, respiratory rate, thoracic impedance, blood oxygen content, carbon dioxide content, or myocardial acceleration.

Next, step 210 determines the duration of the atrial overdrive pacing. The pacing therapy can be continued for a defined period of time, which may be programmed into the device or entered into the device by the caregiver. Alternatively, the pacing duration may be a variable time, such as a percentage of the time between sensed depolarizations during the arrhythmia or a period of time determined by feedback from a sensor. For example, the absolute right or left atrial pressure could be measured after termination of an atrial arrhythmia, or the change in right or left atrial pressure could be measured after termination of an atrial arrhythmia. If either the absolute pressure or the change in pressure exceeds some threshold valve, then overdrive pacing or paired pacing is applied. If the threshold is not met, then therapy is withheld.

After the rate and duration of the atrial overdrive pacing are determined, constant rate overdrive pacing is applied at the determined rate for the determined duration in step 212. Step 214 then uses sensor feedback in the manner described with respect to steps 208 and 210 to determine whether the pacing therapy is optimal. If the pacing therapy is not optimal, the process returns to step 208 to re-determine the overdrive rate and step 210 re-determine the overdrive duration. This cycle of steps 208, 210, 212 and 214 is repeated until optimal pacing parameters are found.

Figure 3:
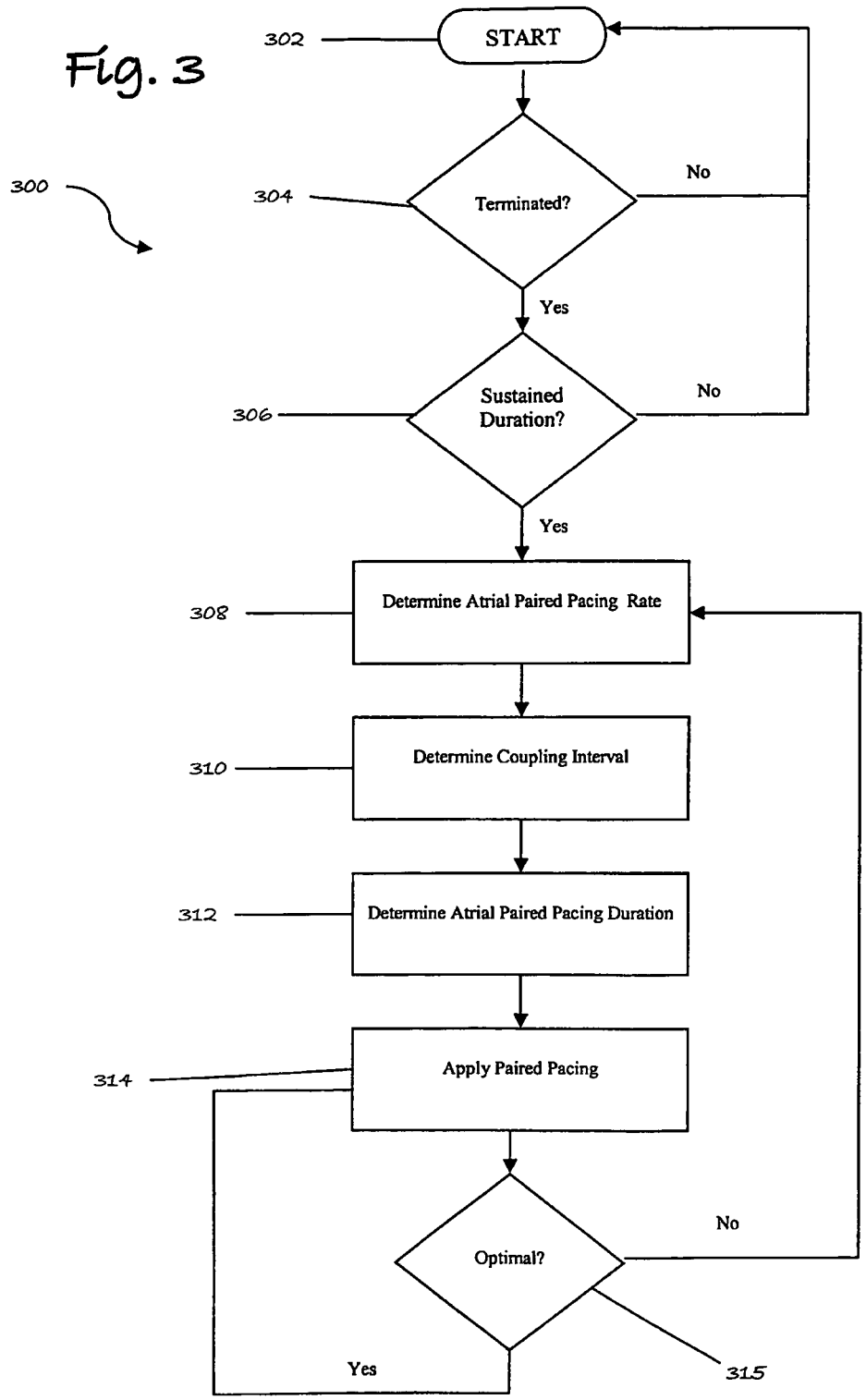
FIG. 3 is a flow diagram illustrating the manner of using transient paired pacing after cardioversion of arrhythmias of a sustained duration of time to reduce the risk of stroke according to an embodiment of the invention.

FIG. 3 shows flow chart 300 for the process of applying transient atrial paired pacing after cardioversion of an arrhythmia of a sustained duration of time to augment atrial mechanical function and reduce the risk of stroke. The process illustrated in FIG. 3 begins at start box 302. Because the process is applied after termination of atrial arrhythmia, decision box 304 determines whether an arrhythmia has terminated. If the arrhythmia has not terminated, the process returns to start box 342; if the arrhythmia has terminated, the process moves on to decision box 306.

Decision box 306 determines whether the episode of atrial arrhythmia occurred for a sustained duration of time. The definition of sustained duration of time could be selected and entered by the caregiver, or alternatively, it could be predetermined and programmed into the device. The duration of time may be defined as the length or percentage of time of a single episode of atrial arrhythmia, or alternatively, as the cumulative length of time of multiple IMD detected arrhythmia during a certain period of time, such as 80%, or 22 hours out of the last 24 hours. If the measured duration of time of the arrhythmia is less than the amount of time defined as a sustained duration of time, the process returns to decision box 304. If the measured duration of time of arrhythmia meets or exceeds the threshold amount of time defined as a sustained duration of time, the process advances to step 308.

Next, step 310 determines the coupling interval. Paired pacing involves the application of a pair of closely coupled pulses: an initial pulse and a second pulse just outside of the refractory period of beat evoked by the initial pulse. The coupling interval is the amount of time between the first and second pulse, or the time between the sensed atrial event and the coupled pace. As with the paired pacing rate, the coupling interval may be pre-set in the device, or it may be based on the paired pacing interval during sinus rhythm or determined by using feedback from a sensor in the same way as described with respect to determining the paired pacing rate in box 308.

Next, step 312 determines the duration of the atrial paired pacing. The pacing therapy could be continued for a defined period of time, which may be programmed into the device or entered into the device by the user. Alternatively, the pacing duration may be a variable time, either a percentage of the duration of the arrhythmia or a period of time determined by feedback from a sensor. Hemodynamic information could also be measured directly by the IMD, or information could be transmitted to the device from another IMD or other device via telemetry. For example, the absolute right or left atrial pressure could be measured after termination of atrial arrhythmia, or the change in right or left atrial pressure could be measured after termination of atrial arrhythmia. If either the absolute pressure or the change in pressure exceeds some threshold valve, then paired pacing therapy is applied. If the threshold is not met, then therapy is withheld. Other hemodynamic variables could be in used in place of, or in addition to, atrial pressure to select the pacing rate, such as arterial pressure, ventricular pressure, mitral valve blood flow, aortic blood flow, left ventricular volume, left ventricular dimension, respiratory rate, thoracic impedance, blood oxygen content, carbon dioxide content, or myocardial acceleration.

After the rate, coupling interval and duration of the atrial paired pacing are determined, atrial paired pacing is applied at step 314. Step 316 then uses sensor feedback in the manner described with respect to steps 308, 310 and 312 to determine whether the pacing therapy is optimal. If the pacing therapy is not optimal, the process returns to step 308 to re-determine the overdrive rate, step 310 to re-determine the coupling interval and step 312 re-determine the paired pacing duration. This cycle of steps 308, 310, 312, 314 and 316 is repeated until optimal pacing parameters are found.

The present invention paces a heart after termination of an arrhythmia of sustained duration in order to reduce the risk of stroke. The invention may be implemented using existing implantable medical devices, which are capable of applying overdrive pacing and paired pacing, and which include sensors that can monitor hemodynamic variables.

Although the present invention has been described with reference to preferred embodiments, workers skilled in the art will recognize that changes may be made in form and detail without departing from the spirit and scope of the invention.

The invention claimed is:

1. An implantable medical device comprising:
a therapy circuit that delivers a cardioversion therapy based, at least in part, on a commencement of an arrhythmia event; and
a control circuit, operatively coupled to the therapy circuit, that:
detects a termination of the arrhythmia event subsequent to the cardioversion therapy;
determines, in response to the termination of the arrhythmia event, whether a duration of the arrhythmia preceding the termination of the arrhythmia event exceeds a predetermined duration time; and
controls the therapy cricuit to deliver a transient pacing therapy following the termination of the arrhythmia event and during a sinus rhythm based on the duration of the arrhythmia if the duration of the arrhythmia exceeds the predetermined duration time;
wherein the control circuit controls the therapy circuit to deliver the transient pacing therapy following the termination of the arrhythmia event and during the sinus rhythm based on the duration of the arrhythmia only if the duration of the arrhythmia exceeds the predetermined duration time.

2. The implantable medical device of claim 1 wherein the transient pacing therapy is overdrive pacing.

3. The implantable medical device of claim 1 wherein the transient pacing therapy is paired pacing.

4. An implantable medical device comprising:
a therapy circuit that delivers cardioversion therapy based, at least in part, on a commencement of an arrhythmia event;
a sensor circuit that measures a parameter; and
a control circuit, operatively coupled to the therapy circuit and the sensor circuit, that:
detects a termination of the arrhythmia event in response to the cardioversion therapy;
determines, in response to the termination of the arrhythmia event, whether a duration of the arrhythmia preceding the termination of the arrhythmia event exceeds a predetermined duration time; and
controls the therapy circuit to deliver a transient pacing therapy following the termination of the arrhythmia and during a sinus rhythm based on the parameter if the duration of the arrhythmia exceeds the predetermined duration time;
wherein the control circuit controls the therapy circuit to deliver the transient pacing therapy following the termination of the arrhythmia event and during the sinus rhythm based on the parameter of the arrhythmia only if the duration of the arrhythmia exceeds the predetermined duration time.

5. The implantable medical device of claim 4 wherein the measured parameter is selected from the group consisting of: atrial pressure, ventricular pressure, mitral valve blood flow, aortic blood flow, left ventricular volume, left ventricular dimension, respiratory rate, thoracic impedance, blood oxygen content, blood carbon dioxide content and myocardial acceleration.

6. The implantable medical device of claim 4 wherein the control circuit uses feedback from the sensor circuit to adjust the transient pacing therapy.

7. The implantable medical device of claim 4 wherein the transient pacing therapy is overdrive pacing.

8. The implantable medical device of claim 4 wherein the pacing therapy is paired pacing.

9. A computer-implemented response system for reducing the risk of stroke after an arrhythmia, the system comprising:
 means for deliverin a cardioversion therapy based at least in part, on a commencement of the arrhythmia;
 means for determining whether the arrhythmia has terminated in response to the cardioversion therapy;
 means for determining, in response to determining the arrhythmia has terminated, whether the arrhythmia preceding the termination of the arrhythmia exceeds a pre-determined sustained duration of time;
 means for selecting, in response to the arrhythmia exceeding the sustained duration of time, a pacing duration;
 means for selecting a pacing rate; and
 means for delivering, subsequent to the termination of the arrhythmia and during a sinus rhythm, a transient pacing therapy at the pacing rate for the pacing duration;
 wherein the means for selecting selects the pacing duration only if the duration of the arrhythmia exceeds the sustained duration of time.

10. The system of claim 9 wherein the pacing duration is a pre-determined fixed time.

11. The system of claim 9 wherein the pacing duration is a percentage of a duration between successive atrial depolarizations of the arrhythmia.

12. The system of claim 9 further comprising:
 means for sensing a physiological parameter with a sensor; and
 means for adjusting the delivering of the second pacing therapy based on the sensed parameter.

13. The system of claim 12 wherein the sensed parameter is selected from the group consisting of: atrial pressure, ventricular pressure, mitral valve blood flow, aortic blood flow, left ventricular volume, left ventricular dimension, respiratory rate, thoracic impedance, blood oxygen content, blood carbon dioxide content and myocardial acceleration.

14. The system of claim 9 wherein the pacing rate is preset.

15. The system of claim 9 further comprising:
 means for using data from a sensor to select the pacing rate.

16. The system of claim 15 wherein the sensor measures a parameter selected from the group consisting of: atrial pressure, ventricular pressure, mitral valve blood flow, aortic blood flow, left ventricular volume, left ventricular dimension, respiratory rate, thoracic impedance, blood oxygen content, blood carbon dioxide content and myocardial acceleration.

17. The system of claim 9 wherein the pacing rate and the pacing duration correspond to overdrive pacing.

18. The system of claim 9 wherein the pacing rate and the pacing duration correspond to paired pacing.

19. The system of claim 18 further comprising means for determining a coupling interval.

20. The system of claim 9 wherein a processor is implanted in cooperation with electronic components of an implantable medical device.

* * * * *

UNITED STATES PATENT AND TRADEMARK OFFICE
CERTIFICATE OF CORRECTION

PATENT NO.          : 8,700,155 B2
APPLICATION NO.     : 11/095846
DATED               : April 15, 2014
INVENTOR(S)         : Douglas A. Hettrick et al.

It is certified that error appears in the above-identified patent and that said Letters Patent is hereby corrected as shown below:

IN THE CLAIMS

Col. 6, line 14, delete "controls the therapy cricuit to deliver" and insert in place thereof -- controls the therapy circuit to deliver --;

Col. 7, line 3, delete "for deliverin a cardioversion therapy based at" and insert in place thereof -- for delivering a cardioversion therapy based, at --.

Signed and Sealed this
Eighth Day of March, 2016

Michelle K. Lee
*Director of the United States Patent and Trademark Office*